(12) United States Patent
Anglese

(10) Patent No.: US 11,179,206 B2
(45) Date of Patent: Nov. 23, 2021

(54) GEARED ACTUATION MECHANISMS FOR SURGICAL INSTRUMENTS SUCH AS FOR USE IN ROBOTIC SURGICAL SYSTEMS

(71) Applicant: COVIDIEN LP, Mansfield, MA (US)

(72) Inventor: Kurt J. Anglese, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 16/261,053

(22) Filed: Jan. 29, 2019

(65) Prior Publication Data

US 2020/0237455 A1 Jul. 30, 2020

(51) Int. Cl.
*A61B 34/30* (2016.01)
*A61B 34/00* (2016.01)
*A61B 17/29* (2006.01)
*A61B 17/00* (2006.01)

(52) U.S. Cl.
CPC ............. *A61B 34/30* (2016.02); *A61B 17/29* (2013.01); *A61B 34/71* (2016.02); *A61B 2017/00398* (2013.01); *A61B 2017/2926* (2013.01); *A61B 2034/305* (2016.02)

(58) Field of Classification Search
CPC ......... A61B 34/30; A61B 34/71; A61B 17/29; A61B 2017/00398; A61B 2034/305; A61B 2017/2926; A61B 34/37; A61B 17/295; A61B 2017/2903; A61B 2018/1455; A61B 18/1445; A61B 34/35
See application file for complete search history.

(56) References Cited

U.S. PATENT DOCUMENTS

| | | |
|---|---|---|
| 5,752,973 A | 5/1998 | Kieturakis |
| 5,792,135 A | 8/1998 | Madhani et al. |
| 5,848,986 A | 12/1998 | Lundquist et al. |
| 6,817,974 B2 | 11/2004 | Cooper et al. |
| 7,799,028 B2 | 9/2010 | Schechter et al. |

(Continued)

FOREIGN PATENT DOCUMENTS

EP 2783653 A1 10/2014

OTHER PUBLICATIONS

Extended European Search Report issued in corresponding European Application No. 20157439.9 dated Jun. 25, 2020, 9 pages.

*Primary Examiner* — Katherine H Schwiker
*Assistant Examiner* — Raihan R Khandker
(74) *Attorney, Agent, or Firm* — Carter, DeLuca & Farrell LLP

(57) ABSTRACT

A surgical instrument configured for use with a robotic surgical system includes a housing, a shaft extending distally from the housing and including an articulating portion, an end effector assembly extending distally from the shaft and including first and second jaw members, a knife configured for translation between the jaw members, and a gearbox assembly disposed within the housing and operably coupled to the articulating portion of the shaft, the end effector assembly, and the knife. The gearbox assembly includes four rotational input gears each adapted to receive a rotational input from a robotic arm. The gearbox assembly is configured to independently articulate the end effector assembly about a first axis, articulate the end effector assembly about a second axis, move the jaw member(s) relative to the other, and translate the knife between the jaw members based upon the rotational inputs received by the four rotational input gears.

20 Claims, 14 Drawing Sheets

(56) References Cited

U.S. PATENT DOCUMENTS

| | | |
|---|---|---|
| 7,861,906 B2 | 1/2011 | Doll et al. |
| 7,918,230 B2 | 4/2011 | Whitman et al. |
| 8,579,176 B2 | 11/2013 | Smith et al. |
| 9,055,961 B2 | 6/2015 | Manzo et al. |
| 9,474,569 B2 | 10/2016 | Manzo et al. |
| 2002/0099371 A1 | 7/2002 | Schulze et al. |
| 2002/0177842 A1 | 11/2002 | Weiss |
| 2003/0125734 A1 | 7/2003 | Mollenauer |
| 2003/0208186 A1 | 11/2003 | Moreyra |
| 2006/0022015 A1 | 2/2006 | Shelton et al. |
| 2006/0025811 A1 | 2/2006 | Shelton |
| 2006/0161138 A1 | 7/2006 | Orban et al. |
| 2007/0233052 A1 | 10/2007 | Brock |
| 2008/0015631 A1 | 1/2008 | Lee et al. |
| 2010/0274265 A1 | 10/2010 | Wingardner et al. |
| 2010/0292691 A1 | 11/2010 | Brogna |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2014/0276723 A1 | 9/2014 | Parihar et al. |
| 2017/0042560 A1 | 2/2017 | Lee et al. |
| 2018/0206904 A1* | 7/2018 | Felder ................ A61B 18/1445 |
| 2020/0129255 A1* | 4/2020 | Kallenberger ......... A61B 34/35 |

* cited by examiner

GEARED ACTUATION MECHANISMS FOR SURGICAL INSTRUMENTS SUCH AS FOR USE IN ROBOTIC SURGICAL SYSTEMS

BACKGROUND

Technical Field

The present disclosure relates to surgical instruments and, more specifically, to geared actuation mechanisms for surgical instruments such as, for example, for use in robotic surgical systems.

Background of Related Art

Robotic surgical systems are increasingly utilized in various different surgical procedures. Some robotic surgical systems included a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be taken in determining how to utilize the available inputs provided by the robotic arm to achieve the desired functionality of the surgical instrument. As can be appreciated, challenges arise when additional functionality is desired while the number, type, and configuration of inputs remains constant.

SUMMARY

As used herein, the term "distal" refers to the portion that is being described which is further from a surgeon, while the term "proximal" refers to the portion that is being described which is closer to a surgeon. The terms "about," "substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is a gearbox assembly of a surgical instrument. The gearbox assembly includes a carriage configured to selectively translate; first, second, third, and fourth gear systems each including an input portion configured to receive an input and an output portion configured to provide an output; a first differential gear assembly operably coupled between the first and second gear systems; a second differential gear assembly operably coupled between the third and fourth gear systems; and a third differential gear assembly operably coupled between the first and second differential gear assemblies. The third differential gear assembly includes an output coupled to the carriage. In response to two gear systems of the first, second, third, and fourth gear systems receiving a different input from the other two gear systems of the first, second, third, and fourth gear systems, the third differential gear assembly provides no output to the carriage. In response to equal inputs provided to each of the first, second, third, and fourth gear systems, the output of the third differential gear assembly translates the carriage.

In an aspect of the present disclosure, each of the first, second, third, and fourth gear systems is configured to receive a rotational input and provide a translational output.

In another aspect of the present disclosure, each of the first, second, third, and fourth gear systems includes an input gear assembly; a transition gear assembly operably coupled to the input gear assembly; and an output gear assembly operably coupled to the transition gear assembly.

In another aspect of the present disclosure, the output gear assembly is a lead screw assembly. Each lead screw assembly may include a lead screw longitudinally fixed and rotatable coupled to the carriage, and a hub operably engaged about the lead screw such that rotation of the lead screw translates the hub. In aspects, the hub is an internally-threaded nut. Further, in aspects, in response to the equal inputs provided to each of the first, second, third, and fourth gear assemblies, the carriage is translated to thereby translate the lead screws opposite the hubs such that the hubs remain relatively stationary.

In still another aspect of the present disclosure, the first differential gear assembly is configured to received inputs from the first and second gear systems and to provide an output equal to an average of the received inputs from the first and second gear systems, the second differential gear assembly is configured to received inputs from the third and fourth gear systems and to provide an output equal to an average of the received inputs from the third and fourth gear systems, and the third differential gear assembly is configured to received inputs from the first and second differential gear systems and to provide an output equal to an average of the received inputs from the first and second differential gear systems.

In yet another aspect of the present disclosure, an outer shell is disposed about the carriage, the first, second, third, and fourth gear systems, and the first, second, and third differential gear assemblies. In such aspects, a proximal face plate may cooperate with the outer shell to enclose the carriage, the first, second, third, and fourth gear systems, and the first, second, and third differential gear assemblies at least partially therein. Further, the proximal face plate may define apertures through which the input portions of the first, second, third, and fourth gear systems extend to enable application of external inputs to the input portions.

In still yet another aspect of the present disclosure, in response to two gear systems of the first, second, third, and fourth gear systems receiving a first input and the other two gear systems of the first, second, third, and fourth gear systems receiving a second, opposite input, the third differential gear assembly provides no output to the carriage. More specifically, in aspects, when the first and second gear systems receive the first input and the third and fourth gear systems receive the second, opposite input, the third differential gear assembly provides no output to the carriage; when the first and third gear systems receive the first input and the second and fourth gear systems receive the second, opposite input, the third differential gear assembly provides no output to the carriage, and/or when the first and fourth gear systems receive the first input and the second and third gear systems receive the second, opposite input, the third differential gear assembly provides no output to the carriage.

A method of operating a gearbox assembly of a surgical instrument including a carriage, first, second, third, and fourth gear systems, a first differential gear assembly operably coupled between the first and second gear systems, a second differential gear assembly operably coupled between the third and fourth gear systems, and a third differential gear assembly operably coupled between the first and second differential gear assemblies is also provided in accordance with aspects of the present disclosure. The method includes providing a first input to two gear systems of the first, second, third, and fourth gear systems and a second, opposite input to the other two gear systems of the first, second, third, and fourth gear systems such that the first, second, third, and fourth gear systems are activated to perform a first function. The method further includes providing an equal input to each of the first, second, third, and fourth gear systems such that the first, second, third, and fourth gear systems are activated and the third differential gear assembly is activated. Activation of the third differential gear assembly performs a second function and cancels out activation of the first, second, third, and fourth gear systems such that the first function is not performed.

In an aspect of the present disclosure, providing the first input and the second, opposite input includes providing the first input to the first and second gear systems and the second, opposite input to the third and fourth gear systems. Alternatively or additionally, providing the first input and the second, opposite input includes providing the first input to the first and third gear systems and the second, opposite input to the second and fourth gear systems. Alternatively or additionally, providing the first input and the second, opposite input includes providing the first input to the first and fourth gear systems and the second, opposite input to the second and third gear systems. With respect to no rotational motion input, the opposite of such is also no rotational motion input.

In another aspect of the present disclosure, when the first function is performed, the second function is not performed.

In yet another aspect of the present disclosure, activation of each of the first, second, third, and fourth gear assemblies provides first, second, third, and fourth translation outputs to perform the first function.

In still another aspect of the present disclosure, activation of the third differential gear assembly provides a translation output to perform the second function. The translation output of the third differential gear assembly is opposite the first, second, third, and fourth translation outputs such that the first, second, third, and fourth translation outputs are canceled out and do not perform the first function.

In still yet another aspect of the present disclosure, the first input, the second, opposite input, and the equal input are rotational inputs.

Another surgical instrument configured for use with a robotic surgical system and provided in accordance with the present disclosure includes a housing, a shaft extending distally from the housing, an end effector assembly extending distally from the shaft, a knife, and a gearbox assembly disposed within the housing. The shaft includes an articulating portion. The end effector assembly extends distally from the shaft and includes first and second jaw members. At least the first jaw member is movable relative to the second jaw member from a spaced-apart position to an approximated position to grasp tissue therebetween. The knife is configured for translation between the jaw members to cut tissue grasped therebetween. The gearbox assembly is operably coupled to the articulating portion of the shaft, the end effector assembly, and the knife. The gearbox assembly includes four rotational input gears each adapted to receive a rotational input from a robotic arm. The gearbox assembly is configured to independently articulate the end effector assembly about a first axis, articulate the end effector assembly about a second axis, move the at least one of the first or second jaw members relative to the other, and translate the knife between the first and second jaw members based upon the rotational inputs received by the four rotational input gears.

In an aspect of the present disclosure, a plurality of articulation cables are operably coupled between the gearbox assembly and the articulating portion of the shaft. The gearbox assembly is configured to selectively push or pull each of the plurality of articulation cables in a first manner to articulate the end effector assembly about the first axis in a first direction.

In another aspect of the present disclosure, the gearbox assembly is configured to selectively push or pull each of the plurality of articulation cables in a second, opposite manner to articulate the end effector assembly about the first axis in a second, opposite direction.

In another aspect of the present disclosure, the gearbox assembly is configured to selectively push or pull each of the plurality of articulation cables in a third manner to articulate the end effector assembly about the second axis in a third direction.

In still another aspect of the present disclosure, the gearbox assembly is configured to selectively push or pull each of the plurality of articulation cables in a fourth manner opposite of the third manner to articulate the end effector assembly about the second axis in a fourth direction opposite of the third direction.

In yet another aspect of the present disclosure, at least two cables of the plurality of cables are operably coupled to the first jaw member. In such aspects, the gearbox assembly is configured to selectively push or pull the at least two cables in a fifth manner to move the first jaw member relative to the second jaw member from the spaced-apart position to the approximated position.

In still yet another aspect of the present disclosure, the gearbox assembly is configured to selectively push or pull the at least two cables in a sixth manner opposite of the fifth manner to move the first jaw member relative to the second jaw member from the approximated position back to the spaced-apart position.

In another aspect of the present disclosure, the surgical instrument further includes a knife cable operably coupled between the gearbox assembly and the knife. The gearbox assembly is configured to selectively push or pull the knife cable to translate the knife between the first and second jaw members.

In an aspect of the present disclosure, in response to similar rotational inputs received by each of the four rotational input gears, the gearbox assembly is configured to translate the knife between the first and second jaw members. Additionally or alternatively, in response to different rotational inputs received by two of the four rotational input gears, the gearbox assembly is configured to articulate the end effector assembly about a first axis, articulate the end effector assembly about a second axis, or move the at least one of the first or second jaw members relative to the other.

The present disclosure also provides a surgical system including a surgical robot including a robotic arm having four rotational outputs, and a surgical instrument configured to couple to the robotic arm and receive the four rotational outputs therefrom. The surgical instrument may be configured in accordance with any of the aspects detailed above or otherwise herein.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
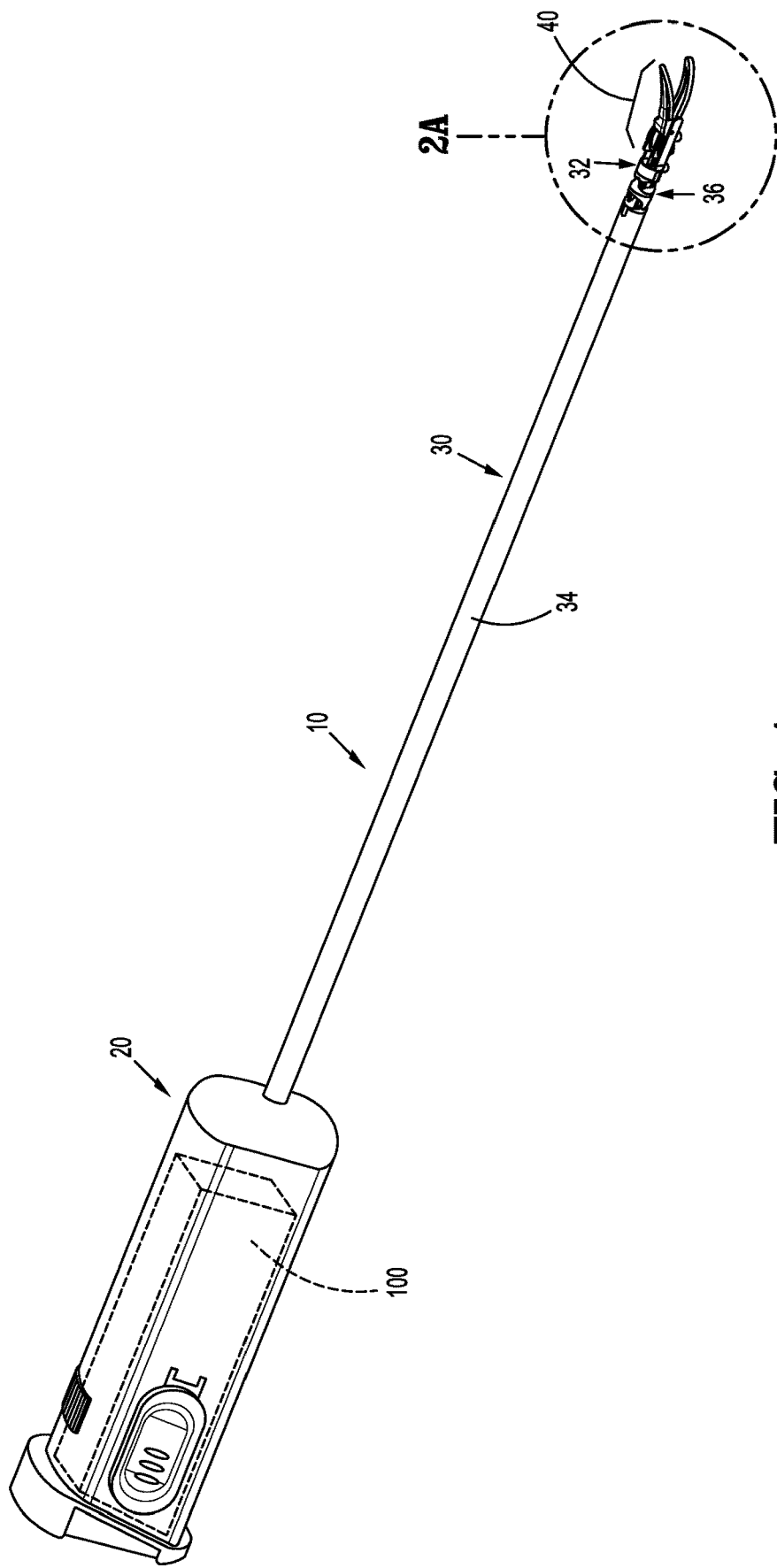
FIG. 1 is a perspective view of a surgical instrument provided in accordance with the present disclosure configured for mounting on a robotic arm of a robotic surgical system.
Figure 2A:
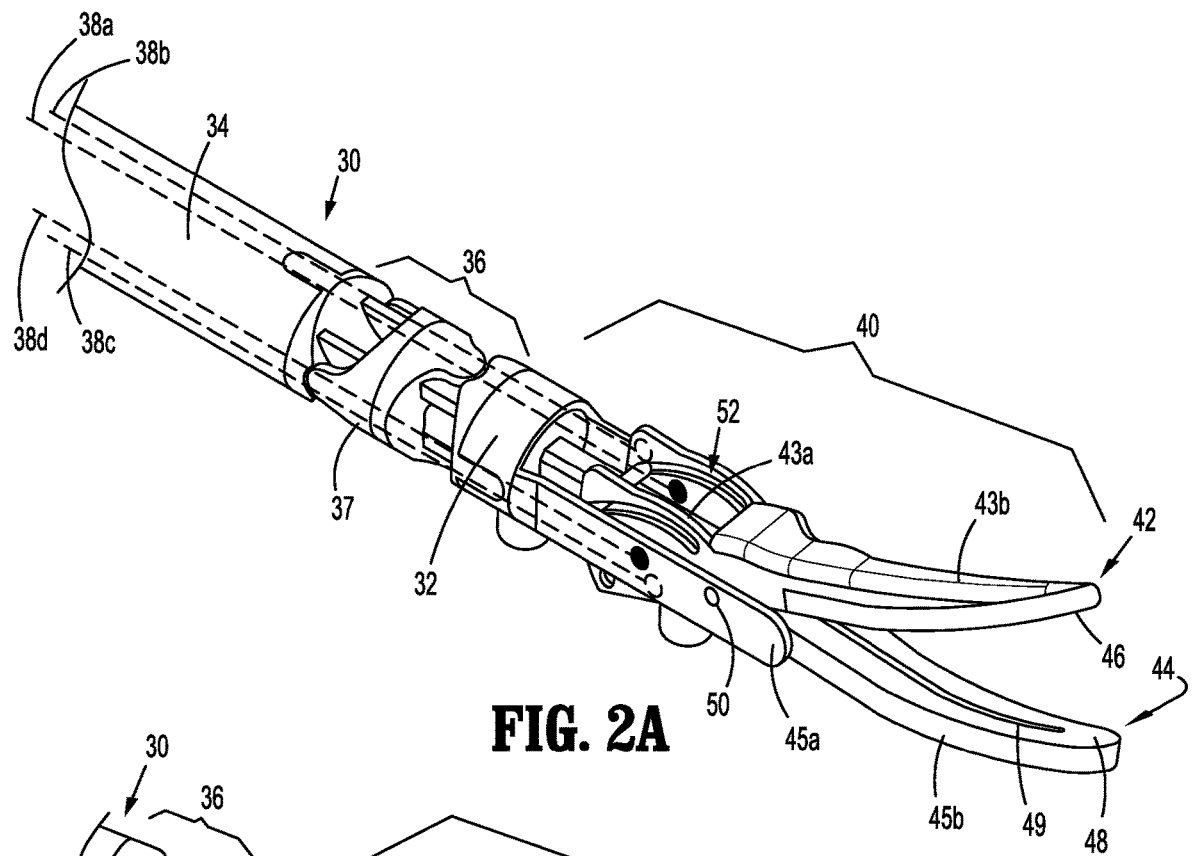
FIG. 2A is an enlarged, perspective view of the area of detail indicated as "2A" in FIG. 1, illustrating an end effector assembly of the surgical instrument of FIG. 1.
Figure 2B:
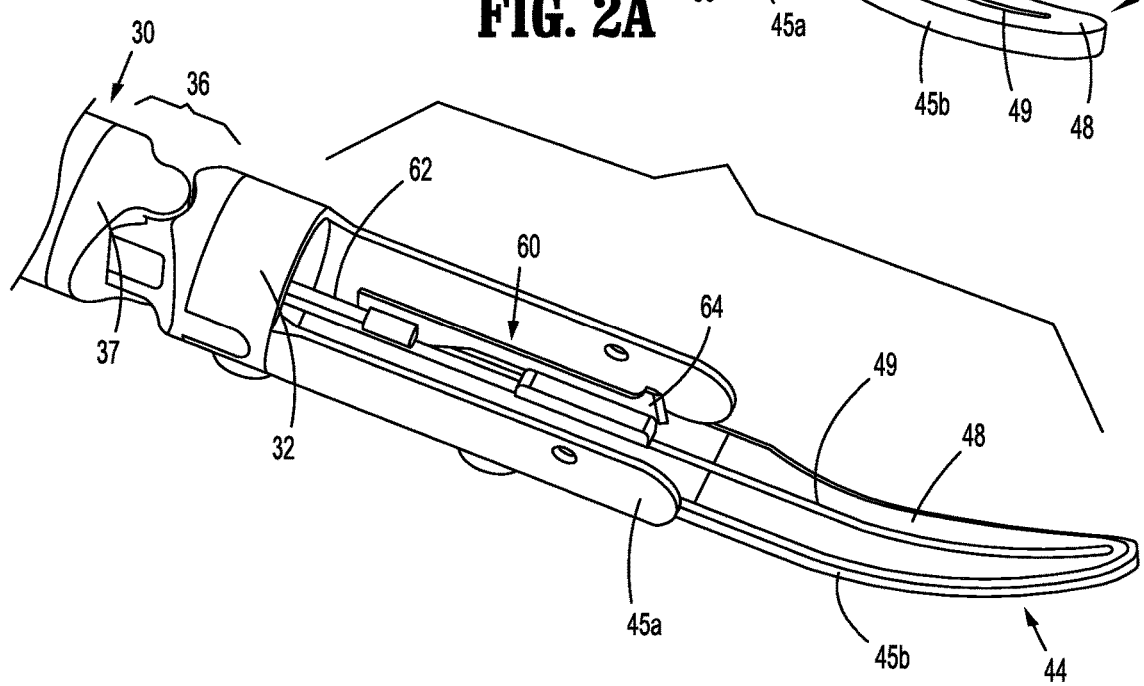
FIG. 2B is an enlarged, perspective view of the end effector assembly of FIG. 2A with one of the jaw members thereof removed.
Figure 3:
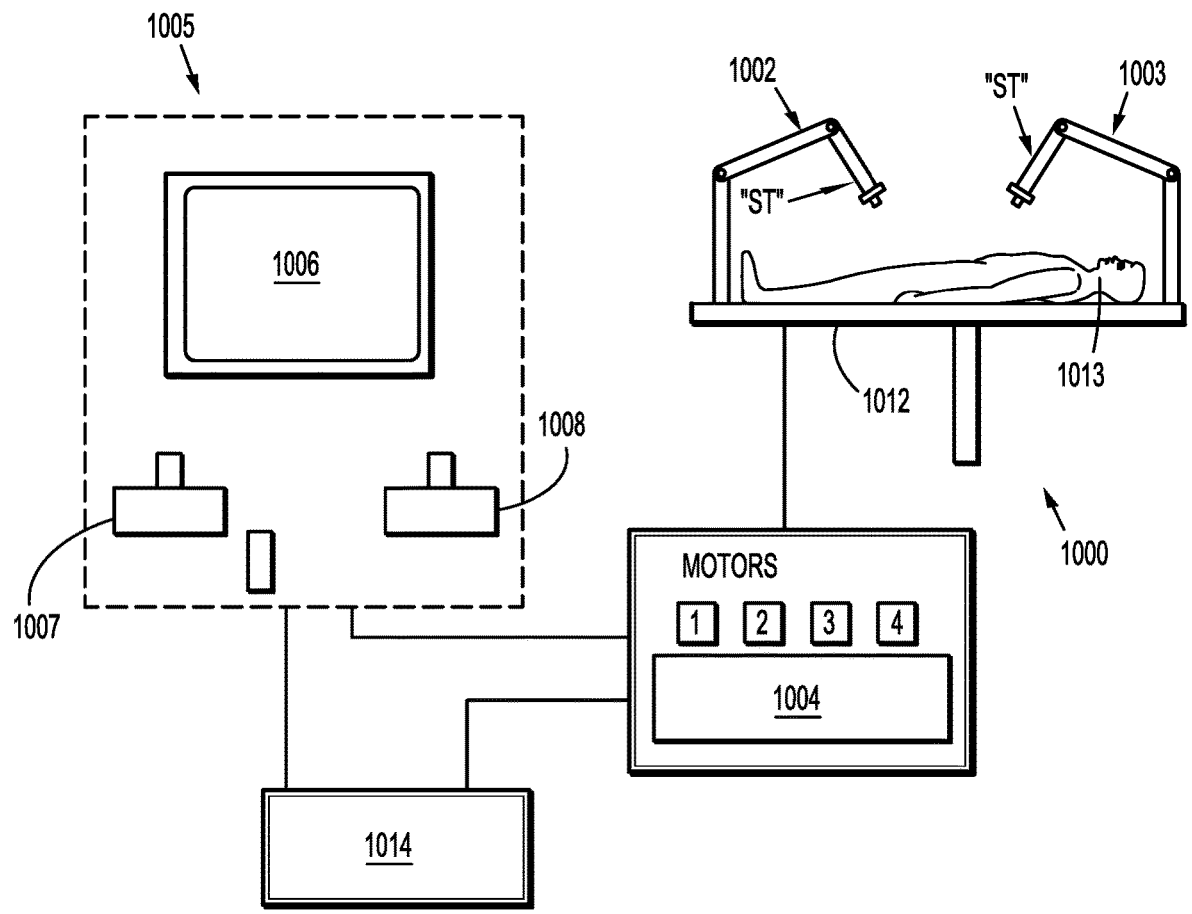
FIG. 3 is a schematic illustration of an exemplary robotic surgical system configured to releasably receive the surgical instrument of FIG. 1.

Referring to FIGS. 1-2B, a surgical instrument 10 provided in accordance with the present disclosure generally includes a housing 20, a shaft 30 extending distally from housing 20, and end effector assembly 40 extending distally from shaft 30, and a gearbox assembly 100 disposed within housing 20 and operably associated with end effector assembly 40. Instrument 10 is detailed herein as an articulating electrosurgical forceps configured for use with a robotic surgical system, e.g., robotic surgical system 1000 (FIG. 3). However, the geared actuation mechanisms of instrument 10 provided in accordance with the present disclosure are equally applicable for use with other suitable surgical instruments and/or in other suitable surgical systems.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38a-38d, e.g., four (4) articulation cables 38a, 38b, 38c, 38d or other suitable actuators, extend through articulating section 36. More specifically, articulation cables 38a-38d are operably coupled to end effector assembly 40 at the distal ends thereof and extend proximally from end effector assembly 40, through distal segment 32 of shaft 30, articulating section 36 of shaft 30, and proximal segment 34 of shaft 30 into housing 20, wherein, as detailed below, articulation cables 38a-38d are operably coupled with gearbox assembly 100 (FIG. 4) to enable selective articulation of distal segment 32 (and, thus end effector assembly 40) relative to proximal segment 34 and housing 20, e.g., about at least two axes of articulation (yaw and pitch articulation, for example), and to enable selective pivoting of jaw members 42, 44 between spaced-apart and approximated positions. Articulation cables 38a-38d are arranged in a generally rectangular or other suitable configuration so as to define an upper right cable 38a, an upper left cable 38b, a lower left cable 38c, and a lower right cable 38d.

Continuing with reference to FIGS. 1-2B end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position and an approximated position for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

A first diagonally-opposed pair of articulation cables, e.g., upper right and lower left articulation cables 38a and 38c, respectively, are operably coupled to end effector assembly 40, e.g., movable jaw member 42 and/or cam-slot assembly 52, in a similar manner, and the other, second diagonally-opposed pair of articulation cables, e.g., upper left and lower right articulation cables 38b and 38d, respectively, are coupled to the end effector assembly 40, e.g., movable jaw member 42 and/or cam-slot assembly 52, in a manner similar to one another but opposite from the manner in which the first diagonally-opposed pair of the articulation cables 38a, 38c are coupled. As such, actuating the first and second diagonally-opposed pairs of articulation cables 38a, 38c and 38b, 38d, respectively, in opposite manners pivots jaw member 42 relative to jaw member 44 between the spaced-apart and approximated positions. More specifically, urging the first pair of articulation cables 38a, 38c proximally and urging the second pair of articulation cables 38b, 38d distally pivots jaw member 42 relative to jaw member 44 towards the approximated position while urging the first pair of articulation cables 38a, 38c distally and urging the second pair of articulation cables 38b, 38d proximally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of diagonal pairs of articulation cables 38a, 38c and 38b, 38d are also contemplated.

With respect to articulation of end effector 40 relative to proximal segment 34 of shaft 30, actuation is again effected in pairs of articulation cables 38a-38d. More specifically, in order to pitch end effector 40, the upper cables, e.g., upper right cable 38a and upper left cable 38b, are actuated in a similar manner while the lower cables, e.g., lower left cable 38c and lower right cable 38d, are actuated in a similar manner relative to one another but an opposite manner relative to the upper cables. With respect to yaw articulation, the right cables, e.g., upper right cable 38a and lower right cable 38d, are actuated in a similar manner while the left cables, e.g., upper left cable 38b and lower left cable 38c, are actuated in a similar manner relative to one another but an opposite manner relative to the right cables.

Referring to FIGS. 2A and 2B, tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment. Instrument 10 (FIG. 1) defines a conductive pathway (not shown) through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue grasped between tissue-contacting surfaces 46, 48.

Longitudinally-extending knife channels 49 (only knife channel 49 of jaw member 44 is illustrated; the knife channel of jaw member 42 is similarly configured) are defined through tissue-contacting surfaces 46, 48, respectively, of jaw members 42, 44. A knife assembly 60 including a knife cable 62 extending from housing 20 through shaft 30 to end effector assembly 40 and a knife blade 64 disposed within end effector assembly 40 between jaw members 42, 44 is provided to enable cutting of tissue grasped between tissue-contacting surfaces 46, 48 of jaw members 42, 44, respectively. Knife cable 62 is operably coupled to gearbox 100 (FIGS. 1 and 4) at a proximal end thereof, as detailed below, to enable selective actuation thereof to, in turn, reciprocate knife blade 64 between jaw members 42, 44 and through knife channels 49 thereof to cut tissue grasped between tissue-contacting surfaces 46, 48.

With additional reference to FIG. 1, as noted above, and as described in greater detail below, gearbox assembly 100 is disposed within housing 20 and operably coupled to articulation cables 38a-38d as well as knife cable 62 to enable selective articulation of end effector assembly 40, pivoting of one or both jaw members 42, 44 between the spaced-apart and approximated positions, and reciprocation of knife blade 64 between jaw members 42, 44. Gearbox assembly 100 is configured to operably interface with a robotic surgical system 1000 (FIG. 3) when instrument 10 is mounted on robotic surgical system 1000 (FIG. 3), to enable robotic operation of gearbox assembly 100 to provide the above-detailed functionality. However, it is also contemplated that gearbox assembly 100 be configured to interface with any other suitable surgical system, e.g., a manual surgical handle, a powered surgical handle, etc. For the purposes herein, robotic surgical system 1000 (FIG. 3) is generally described.

Turning to FIG. 3, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and mounted device which may be, for example, a surgical tool "ST." One or more of the surgical tools "ST" may be instrument 10 (FIG. 1), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Turning now to FIGS. 4-17, gearbox assembly 100 is shown. Gearbox 100, as detailed below, is configured to operably connect to robotic surgical system 1000 (FIG. 3) and, more specifically, to four rotational outputs (not shown) of robotic surgical system 1000 (FIG. 3), that enable driving of gearbox assembly 100 to independently articulate end effector assembly 40 in pitch and yaw directions, pivot one or both jaw members 42, 44 between the spaced-apart and approximated positions, and reciprocate of knife blade 64 between jaw members 42, 44 (see FIGS. 2A and 2B).

Referring to FIGS. 4-8, gearbox assembly 100 generally includes an outer shell 102, a proximal face plate 104, four input gear assemblies 112, 114, 116, 118, four transition gear assemblies 132, 134, 136, 138, four lead screw assemblies 152, 154, 156, 158, a drive carriage assembly 170, and three differential gear assemblies 182, 184, 186. Outer shell 102 and proximal face plate 104 cooperate to define a housing that encloses the components of gearbox assembly 100 therein.

The four input gear assemblies 112, 114, 116, 118 of gearbox assembly 100 are arranged in a generally rectangular, e.g., square, pattern, although other configurations are also contemplated. Input gear assemblies 112, 114, 116, 118 are similar to one another and, thus, the components and features thereof are collectively detailed below in the singular. Each input gear assembly 112, 114, 116, 118 includes a drive gear 122 extending through an aperture 106 defined within proximal face plate 104. Drive gear 122 is configured to engage a rotational output (not shown) of robotic surgical system 1000 (FIG. 3) such that rotational driving of the rotational output effects similar rotation of drive gear 122. Drive gear 122 is mounted on an input drive shaft 124 towards a proximal end thereof. A compound input gear 126 is mounted on input drive shaft 124 towards a distal end thereof such that, upon rotation imparted to drive gear 122, e.g., via the rotational output (not shown) of robotic surgical system 1000 (FIG. 3), compound input gear 126 is rotated similarly. Compound input gear 126 includes a first gear portion 127 and a second gear portion 129.

Each transition gear assembly 132, 134, 136, 138 is operably associated with one of the input gear assemblies 112, 114, 116, 118, respectively. Transition gear assemblies 132, 134, 136, 138 are similar to one another and, thus, the components and features thereof are collectively detailed below in the singular. Each transition gear assembly 132, 134, 136, 138 includes a proximal gear 142 disposed in meshed engagement with the first gear portion 127 of the compound input gear 126 of the corresponding input gear assembly 112, 114, 116, 116, respectively. Proximal gear 142 is mounted on a transition drive shaft 144 towards a proximal end thereof. An elongated gear 146 is mounted on transition drive shaft 144 towards a distal end thereof such that, upon rotation imparted to proximal gear 142, elongated gear 146 is rotated similarly.

Continuing with reference to FIGS. 4-8, each lead screw assembly 152, 154, 156, 158 is operably associated with one of the transition gear assemblies 132, 134, 136, 138. Lead screw assemblies 152, 154, 156, 158 are similar to one another and, thus, the components and features thereof are collectively detailed below in the singular. Each lead screw assembly 152, 154, 156, 158 includes a lead screw 162 longitudinally fixed but rotatably coupled to drive carriage assembly 170 at the proximal end of the lead screw 162. A hub 164 is threadingly engaged about the lead screw 162 such that rotation of the lead screw 162 translates hub 164 along the lead screw 162. The hub 164 of each lead screw assembly 152, 154, 156, 158 includes a receptacle 166 configured to capture the proximal end of one of the articulation cables 38a, 38b 38c, 38d (FIG. 2A), respectively. In this manner, translation of hub 164 distally along the corresponding lead screw 162 urges the corresponding articulation cable 38a, 38b 38c, 38d (FIG. 2A) distally while translation of hub 164 proximally along the corresponding lead screw 162 urges the corresponding articulation cable 38a, 38b 38c, 38d (FIG. 2A) proximally.

A lead screw gear 168 is fixedly mounted on lead screw 162 towards the proximal end thereof. Lead screw gear 168 is disposed in meshed engagement with the elongated gear 146 of the corresponding transition gear assemblies 132, 134, 136, 138.

Drive carriage assembly 170 includes a housing 172 defining four elongated bores 174 therethrough, each configured to receive the proximal end portion of one of the lead screw assemblies 152, 154, 156, 158, including the lead screw gear 168 thereof. Housing 172 further defines four slots 176 providing transverse access through housing 172 to bores 174, thus enabling the externally-disposed elongated gears 146 of transition gear assemblies 132, 134, 136, 138 to meshingly engage the internally-disposed lead screw gears 168 of lead screw assemblies 152, 154, 156, 158, respectively via slots 176. As noted above, the proximal end portions of lead screws 162 are longitudinally fixed within housing 172 but permitted to rotate relative thereto.

Figure 4:
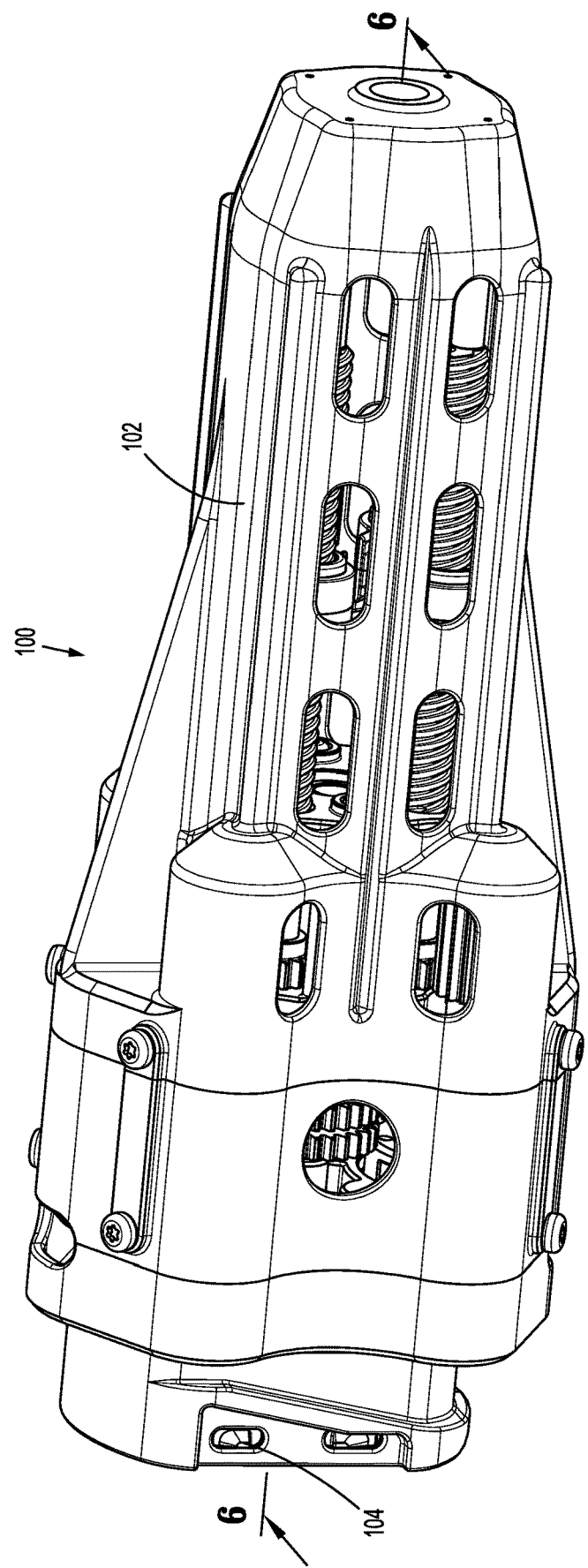
FIG. 4 is a perspective view of a gearbox assembly of the surgical instrument of FIG. 1.

Housing 172 of drive carriage assembly 170 further includes a central lumen 178 defined therethrough. Central lumen 178 is threaded and configured to threadingly receive threaded drive 238 of third differential gear assembly 186 therein such that rotational driving of threaded drive 238 urges housing 172 to longitudinally translate about threaded drive 238 and relative to outer shell 102 (FIG. 4). Longitudinal translation of housing 172 likewise translates lead screws 162 in a similar manner. Further, a proximal end of knife cable 62 (FIG. 2B) is engaged to housing 172 in any suitable manner such that translation of housing 172 similarly urges knife cable 62 (FIG. 2B) to translate, thereby enabling reciprocation of knife blade 64 through jaw members 42, 44 (see FIGS. 2A and 2B).

The three differential gear assemblies 182, 184, 186 are arranged such that first and second differential gear assemblies 182, 184 are proximally-disposed to serve as a first-stage differential while third differential gear assembly 186 is distally-disposed to serve as a second-stage differential. Differential gear assemblies 182, 184, 186 are configured to each include two rotational inputs 192, 194 and a single rotational output 196, wherein the rotational output 196 is equal to the average of the rotational inputs 192, 194. Differential gear assemblies 182, 184, 186 are similar to one another and, thus, the components and features thereof are collectively detailed below in the singular.

With reference to FIGS. 9-14, each differential gear assembly 182, 184, 186 includes a housing 200 formed from first and second housing components 202, 204 secured to one another via screws 205 or in any other suitable manner. Rotational output 196 is fixedly engaged with, e.g., monolithically formed as part of, second housing component 204 such that rotation of housing 200 effects rotation of rotational output 196. Each differential gear assembly 182, 184, 186 further includes a central gear assembly 206 including an inner shaft 208 and an outer sleeve 212. Inner shaft 208 includes first rotational input 192 fixedly engaged with, e.g., monolithically formed as part of, the proximal end thereof and a first inner gear 210 fixedly engaged thereabout towards a distal end thereof. First rotational input 192 protrudes proximally from first housing component 202 of housing 200 while first inner gear 210 is disposed within housing 200. Outer sleeve 212 is rotatably disposed about inner shaft 208 and includes second rotational input 194 fixedly engaged with, e.g., monolithically formed as part of, the proximal end thereof and a second inner gear 214 fixedly engaged thereabout towards a distal end thereof. Second rotational input 194 protrudes proximally from first housing component 202 of housing 200 and first rotational input 194 while second inner gear 210 is disposed within housing 200.

Each differential gear assembly 182, 184, 186 further includes a first set of three radial spur gears 216, 218, 220 and a second set of three radial spur gears 222, 224, 226. The first set of three radial spur gears 216, 218, 220 are disposed within housing 200 and radially arranged about and in meshed engagement with first inner gear 210. The second set of three radial spur gears 222, 224, 226 are disposed within housing 200 and radially arranged about and in meshed engagement with second inner gear 214. Further, the first and second sets of three radial spur gears define adjacent pair of spur gears 216 and 222, 218 and 224, and 220 and 226 that are disposed in meshed engagement with one another.

As a result of the above-detained configurations of differential gear assemblies 182, 184, 186, when the inputs provided to rotational inputs 192, 194 are equal in magnitude and direction, rotational output 196 is driven to rotate with the same magnitude and direction. On the other hand, when the inputs provided to rotational inputs 192, 194 are equal in magnitude but opposite in direction, they are canceled out such that rotational output 196 does not rotate.

Figure 5:
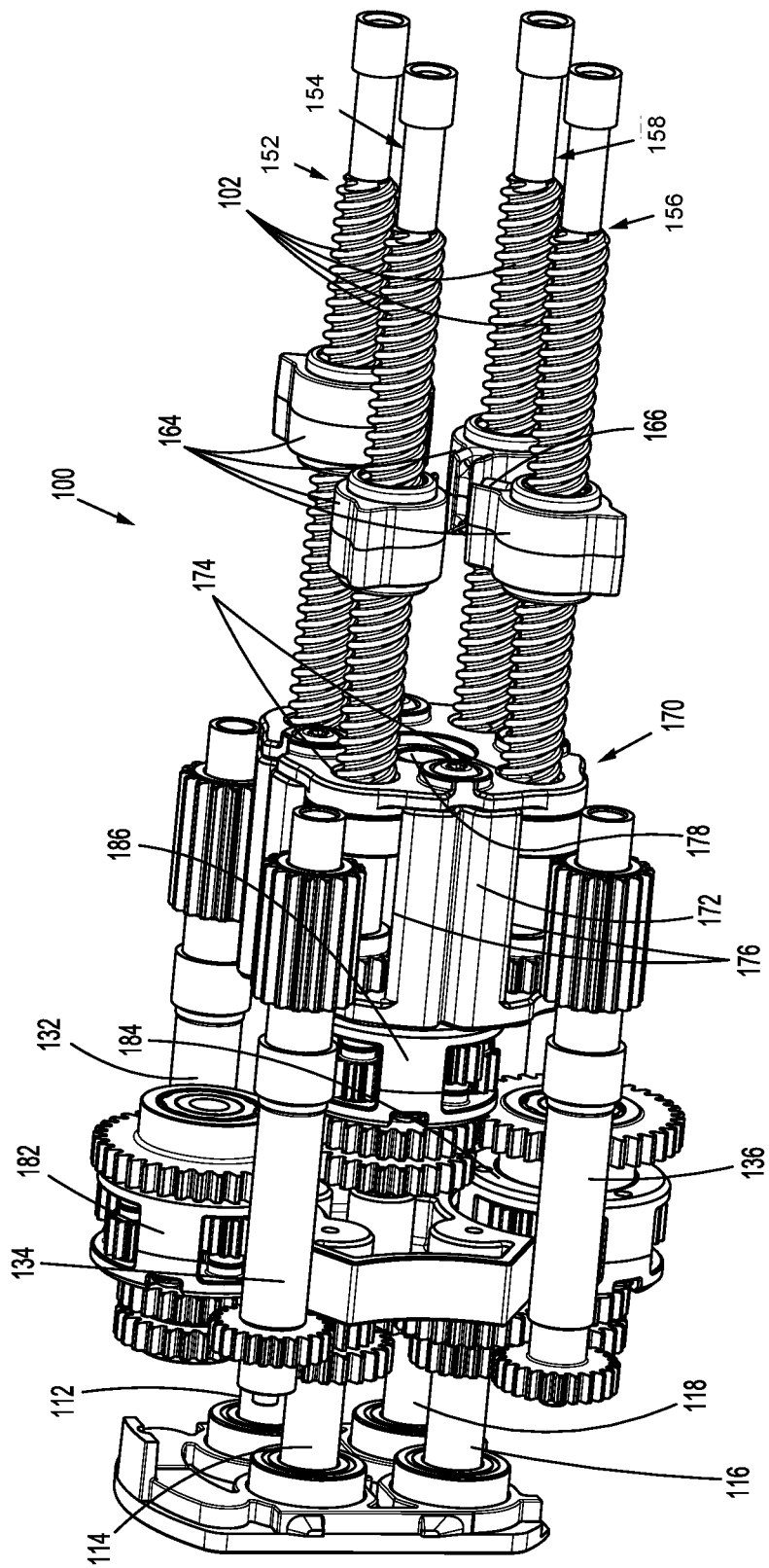
FIG. 5 is a perspective view of the gearbox assembly of FIG. 4 with an outer shell removed.
Figure 6:
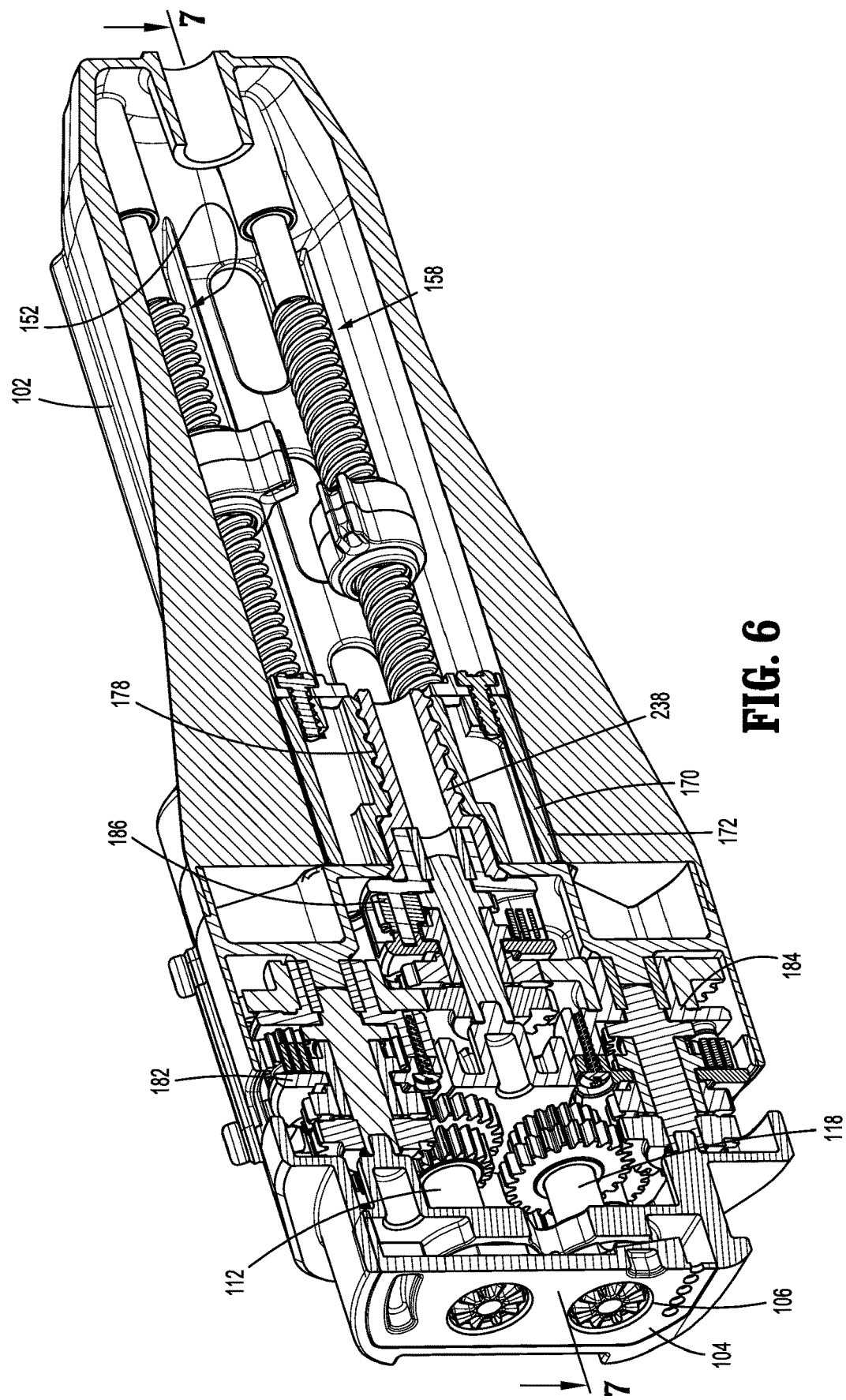
FIG. 6 is a longitudinal, cross-sectional view taken along section line "6-6" of FIG. 4.
Figure 7:
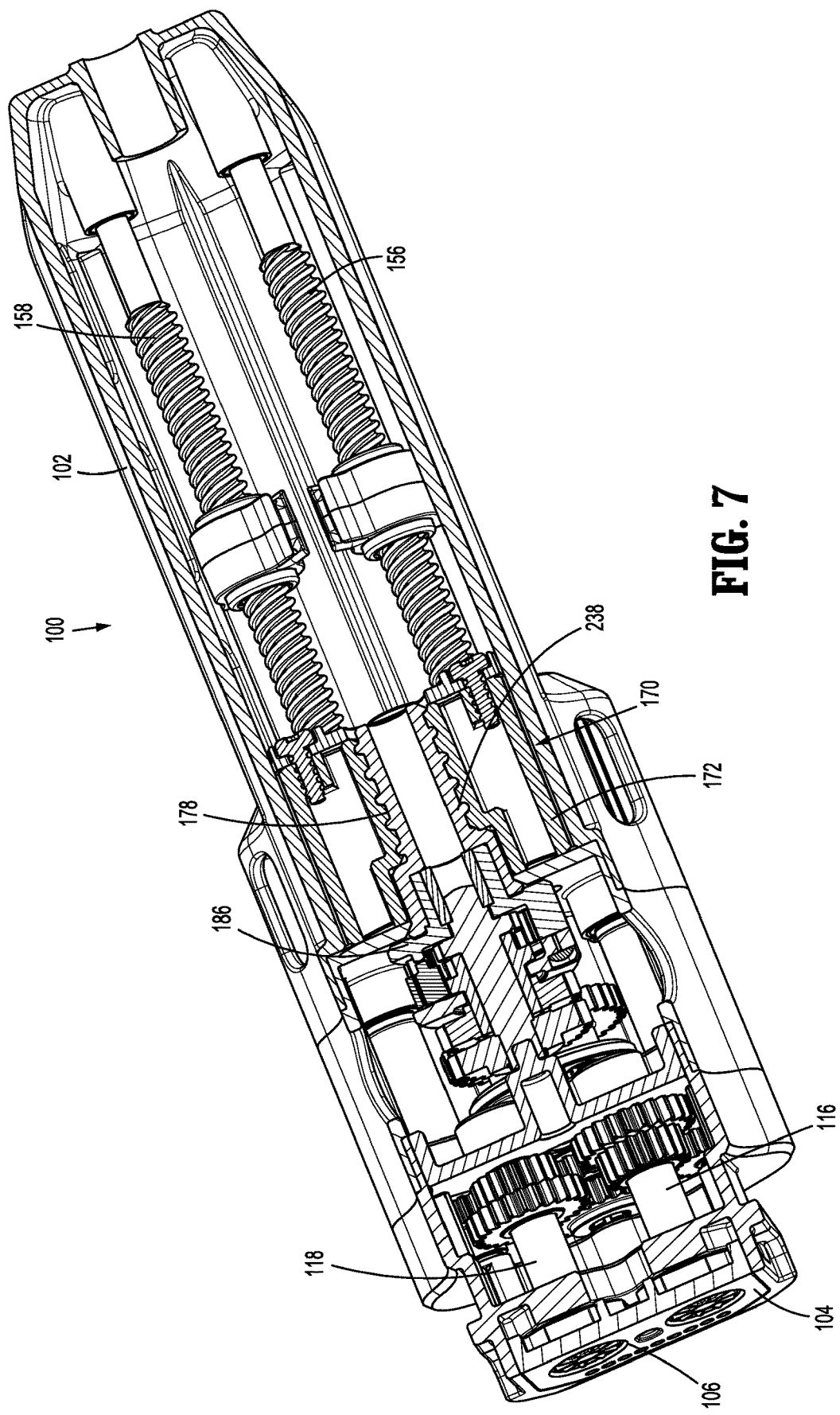
FIG. 7 is a longitudinal, cross-sectional view taken along section line "7-7" of FIG. 6.
Figure 8:
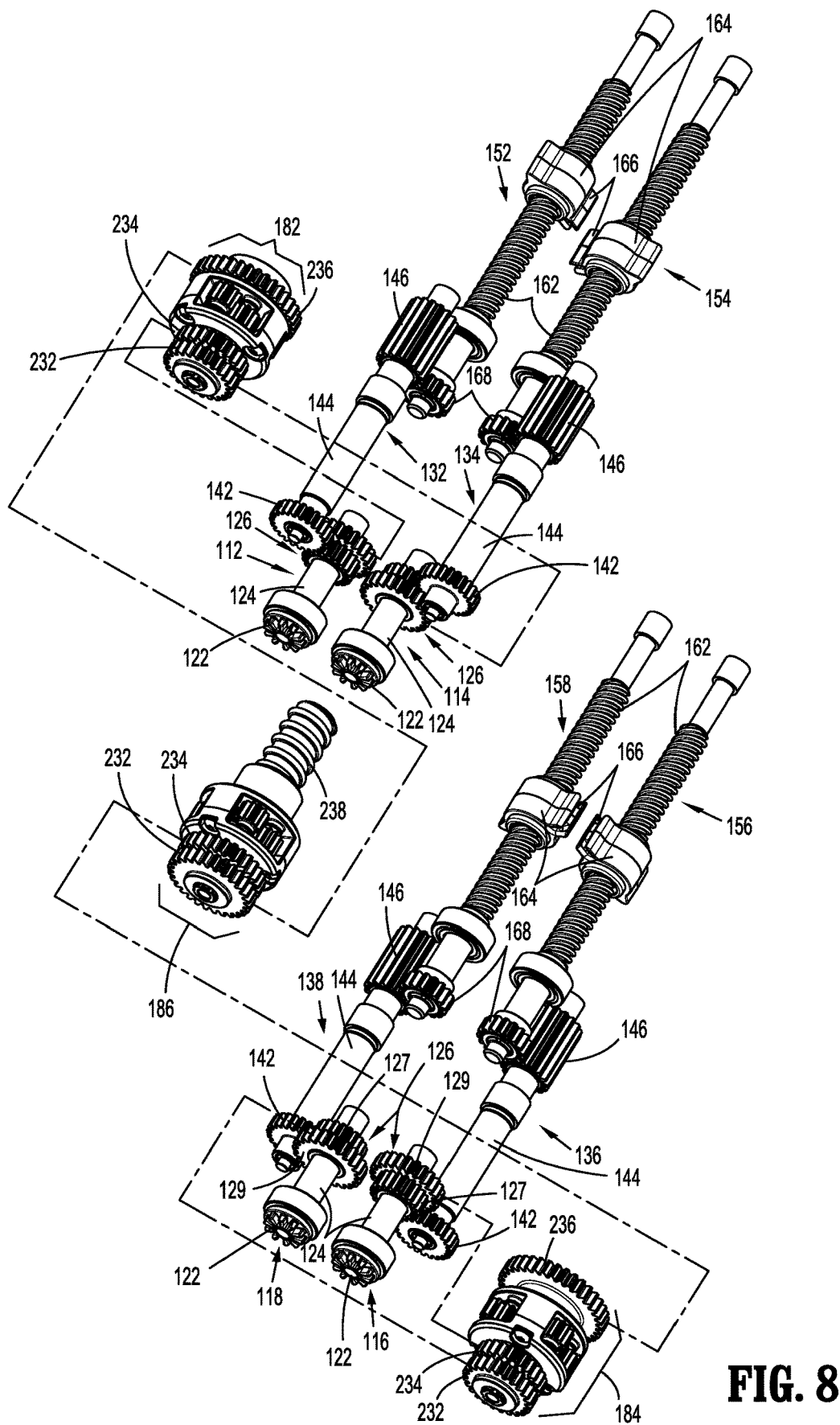
FIG. 8 is an exploded, perspective view of interior gearbox components of the gearbox assembly of FIG. 4.
Figure 9:
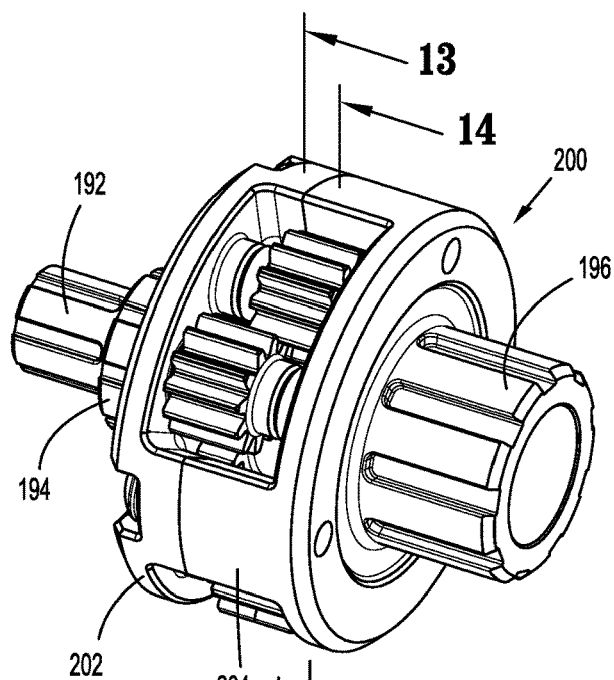
FIG. 9 is a front, perspective view of one differential assembly of the gearbox assembly of FIG. 4.
Figure 10:
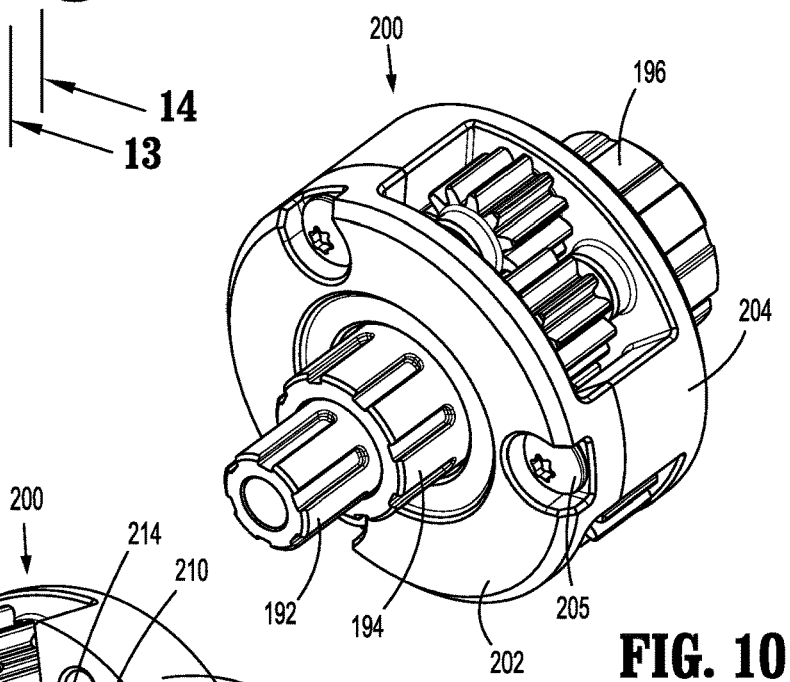
FIG. 10 is a rear, perspective view of the differential assembly of FIG. 9.
Figure 11:
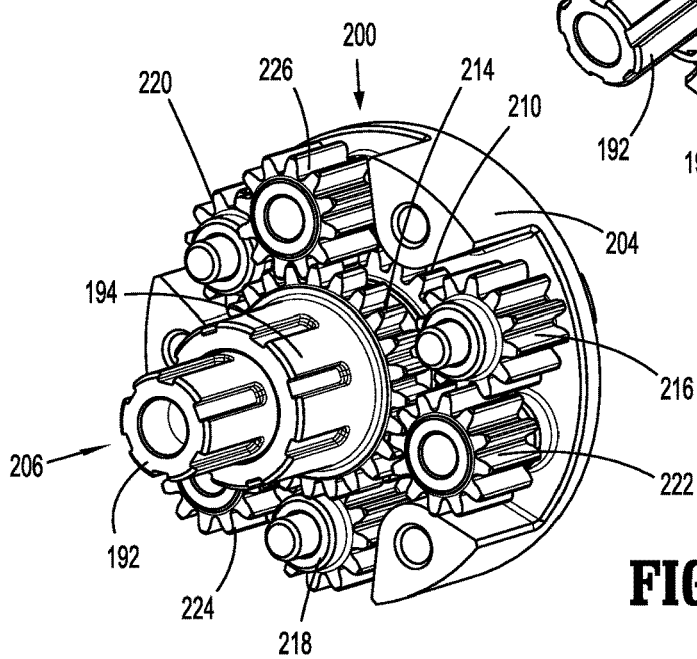
FIG. 11 is a rear, perspective view of the differential assembly of FIG. 9 with a housing portion thereof removed.
Figure 12:
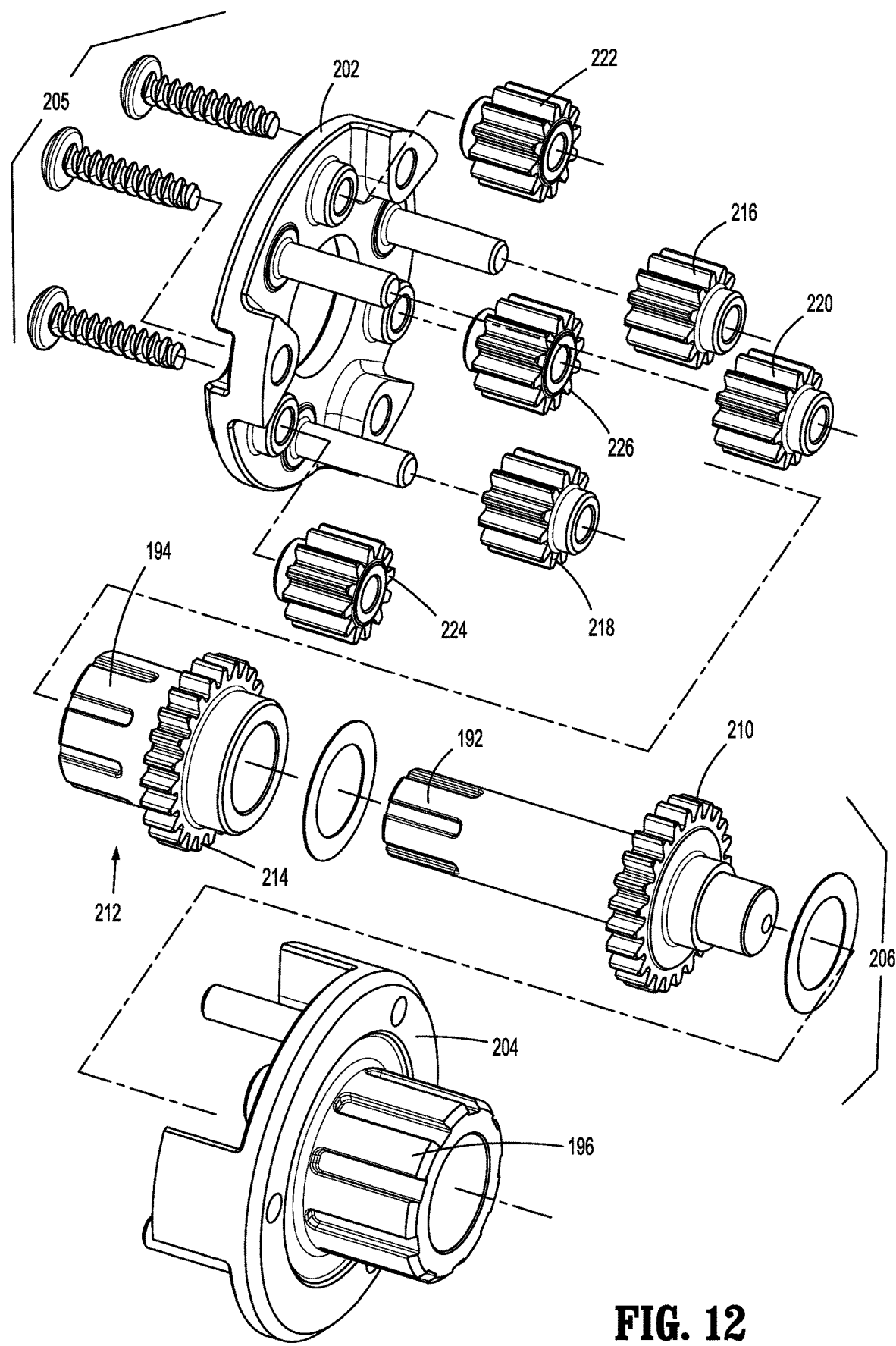
FIG. 12 is an exploded, front, perspective view of the differential assembly of FIG. 9.
Figure 13:
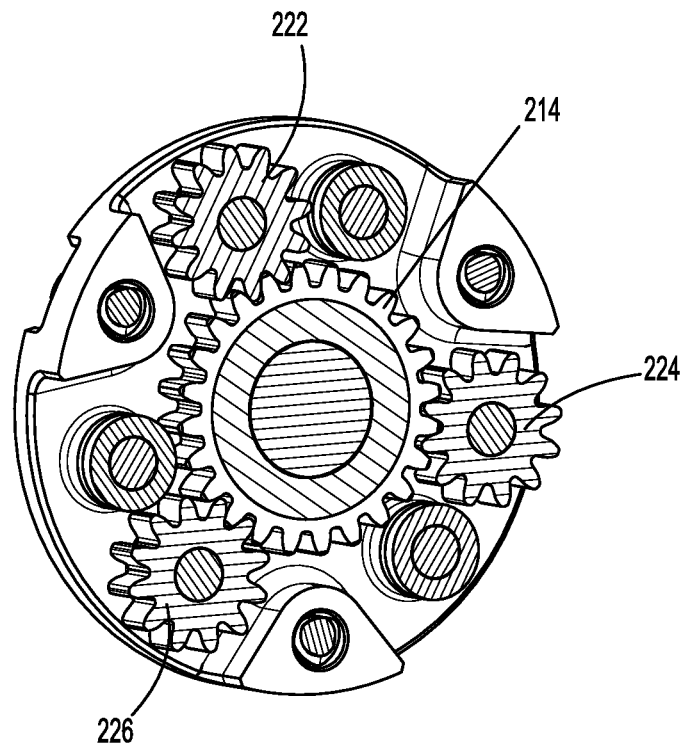
FIG. 13 is a transverse, cross-sectional view taken along section line "13-13" of FIG. 9.
Figure 14:
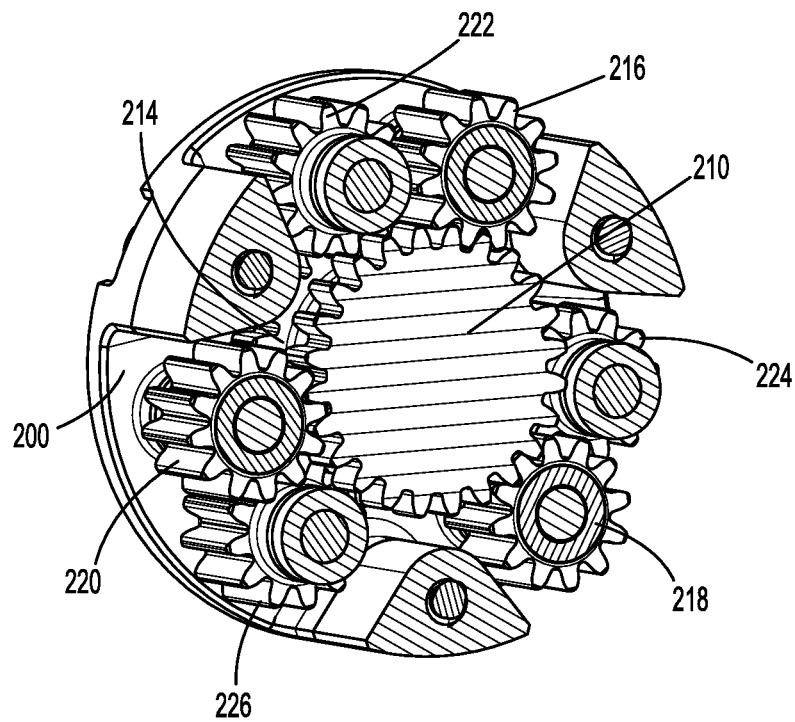
FIG. 14 is a transverse, cross-sectional view taken along section line "14-14" of FIG. 9.

With additional reference to FIGS. 5 and 8, each differential gear assembly 182, 184, 186 includes first and second differential input gears 232, 234 engaged about the first and second rotational inputs 192, 194, respectively, thereof. First differential input gear 232 of first differential gear assembly 182 is disposed in meshed engagement with the second gear portion 129 of the compound input gear 126 of the first input gear assembly 112; second differential input gear 234 of first differential gear assembly 182 is disposed in meshed engagement with the second gear portion 129 of the compound input gear 126 of the second input gear assembly 114; first differential input gear 232 of second differential gear assembly 184 is disposed in meshed engagement with the second gear portion 129 of the compound input gear 126 of the third input gear assembly 116; and second differential input gear 234 of second differential gear assembly 184 is disposed in meshed engagement with the second gear portion 129 of the compound input gear 126 of the fourth input gear assembly 118.

Each of the first and second differential gear assemblies 182, 184 further includes a differential output gear 236 engaged about the rotational output 196 thereof. Differential output gear 236 of first differential gear assembly 182 is disposed in meshed engagement with the first differential input gear 232 of third differential gear assembly 186, while differential output gear 236 of second differential gear assembly 184 is disposed in meshed engagement with the second differential input gear 234 of third differential gear assembly 186. Third differential gear assembly 186 includes a threaded drive 238 engaged about rotational output 196 thereof. Threaded drive 238, as detailed above, is threadingly engaged within central lumen 178 of housing 172 of drive carriage assembly 170.

Figure 15:
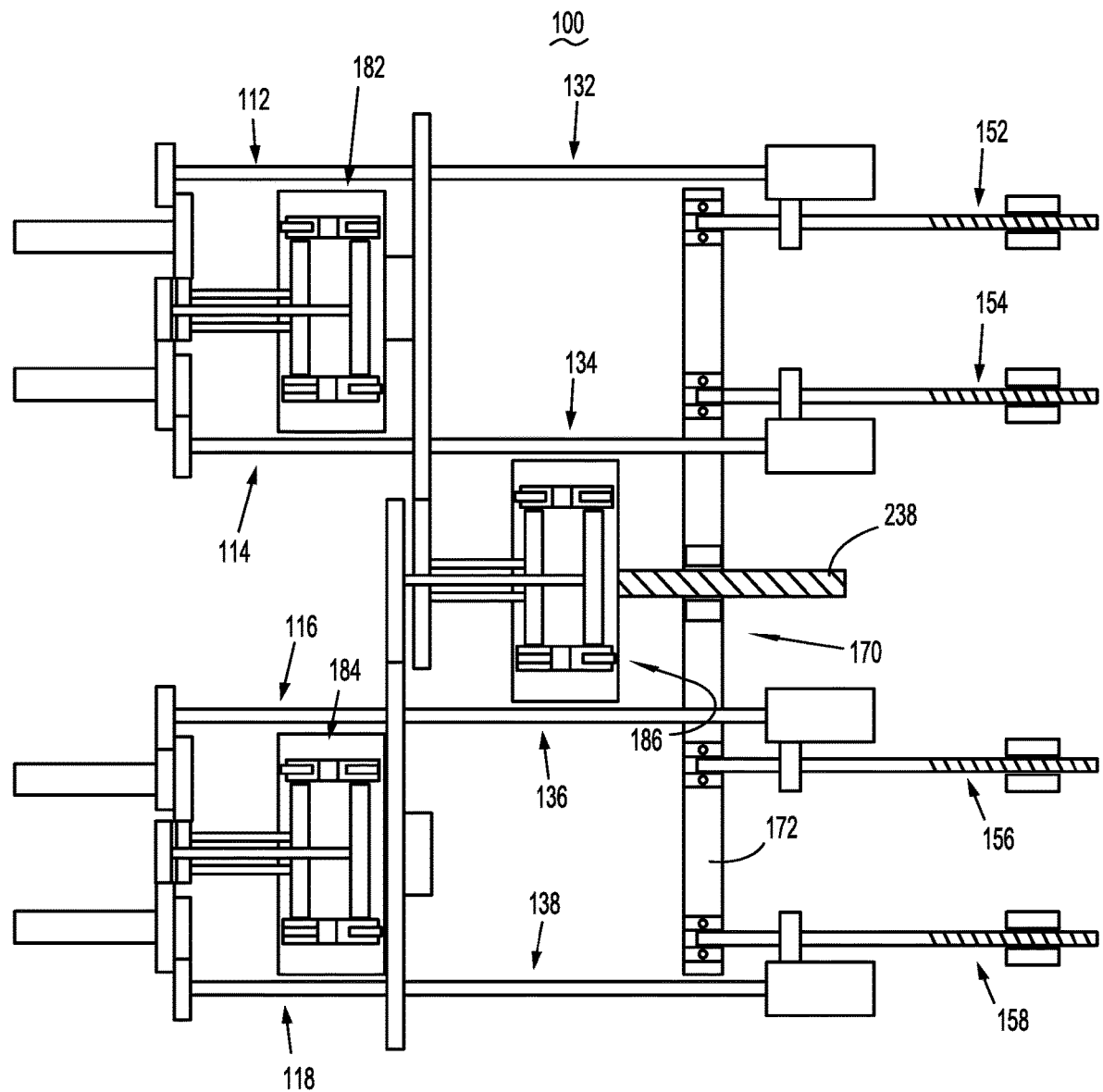
FIG. 15 is a schematic illustration of the interior gearbox components of the gearbox assembly of FIG. 4.

Turning now to FIG. 15, the operation of gearbox assembly 100 is detailed. With respect to upward pitch articulation, input from robotic surgical system 1000 (FIG. 3) is provided to drive rotation of drive gears 122 of input gear assemblies 112, 114 similarly in a first direction and to drive rotation of drive gears 122 of input gear assemblies 116, 118 similarly in a second, opposite direction. As a result of the driving of drive gears 122 of input gear assemblies 112, 114 similarly in the first direction, transition gear assemblies 132, 134 are driven to rotate in the second, opposite direction to, in turn, drive lead screw assemblies 152, 154 to rotate in the first direction, translating the hubs 164 thereof proximally and, thus, pulling articulation cables 38a, 38b proximally. As a result of the driving of drive gears 122 of input gear assemblies 116, 118 similarly in the second direction, transition gear assemblies 136, 138 are driven to rotate in the first direction to, in turn, drive lead screw assemblies 156, 158 to rotate in the second direction, translating the hubs 164 thereof distally and, thus, pushing articulation cables 38c, 38d distally. In this manner, end effector assembly 40 (FIGS. 1-2B) is pitched upwardly.

The similar rotational driving of input gear assemblies 112, 114 provides equal inputs to first differential gear assembly 182 and, thus, an output equal to that input. The similar rotational driving of input gear assemblies 116, 118 provides equal inputs to second differential gear assembly 184 and, thus, an output equal to that input. Further, the output of first differential gear assembly 182 and the output of second differential gear assembly 182, both of which are input to third differential gear assembly 186, are equal in magnitude but opposite in direction and, thus, cancel each other out such that no output is provided from third differential gear assembly 186.

With respect to downward pitch articulation, input from robotic surgical system 1000 (FIG. 3) is provided to drive rotation of drive gears 122 of input gear assemblies 112, 114 similarly in the second direction and to drive rotation of drive gears 122 of input gear assemblies 116, 118 similarly in the first direction. The result is the opposite as that detailed above with respect to upward pitch articulation. That is, hubs 164 of lead screw assemblies 152, 154 are translated distally to push articulation cables 38a, 38b distally and hubs 164 of lead screw assemblies 156, 158 are translated proximally to pull articulation cables 38c, 38d proximally, thereby pitching end effector assembly 40 (FIGS. 1-2B) downwardly. Similarly as above, no output is provided from third differential gear assembly 186.

With respect to right yaw articulation, input from robotic surgical system 1000 (FIG. 3) is provided to drive rotation of drive gears 122 of input gear assemblies 112, 118 similarly in the first direction and to drive rotation of drive gears 122 of input gear assemblies 114, 116 similarly in the second direction. As a result of the driving of drive gears 122 of input gear assemblies 112, 118 similarly in the first direction, transition gear assemblies 132, 138 are driven to rotate in the second, opposite direction to, in turn, drive lead screw assemblies 152, 158 to rotate in the first direction, translating the hubs 164 thereof proximally and, thus, pulling articulation cables 38a, 38d proximally. As a result of the driving of drive gears 122 of input gear assemblies 114, 116 similarly in the second direction, transition gear assemblies 134, 136 are driven to rotate in the first direction to, in turn, drive lead screw assemblies 154, 156 to rotate in the second direction, translating the hubs 164 thereof distally and, thus, pushing articulation cables 38b, 38c distally. In this manner, end effector assembly 40 (FIGS. 1-2B) is yawed to the right.

The opposite rotational driving of input gear assemblies 112, 114 provides opposite inputs to first differential gear assembly 182 and, thus, no output. Likewise, the opposite rotational driving of input gear assemblies 116, 118 provides opposite inputs to second differential gear assembly 184 and, thus, no output. Since neither first differential gear assembly 182 nor second differential gear assembly 184 provides an output, third differential gear assembly 186 receives no input and, thus, provides no output.

With respect to left yaw articulation, input from robotic surgical system 1000 (FIG. 3) is provided to drive rotation of drive gears 122 of input gear assemblies 112, 118 similarly in the second direction and to drive rotation of drive gears 122 of input gear assemblies 114, 116 similarly in the first direction. The result is the opposite as that detailed above with respect to right jaw articulation. That is, hubs 164 of lead screw assemblies 152, 158 are translated distally to push articulation cables 38a, 38d distally and hubs 164 of lead screw assemblies 154, 156 are translated proximally to pull articulation cables 38c, 38d proximally, thereby yawing end effector assembly 40 (FIGS. 1-2B) to the left. Similarly as above, no output is provided from third differential gear assembly 186.

With respect to approximating jaw members 42, 44 of end effector assembly 40 (see FIGS. 1-2B), input from robotic surgical system 1000 (FIG. 3) is provided to drive rotation of drive gears 122 of input gear assemblies 112, 116 similarly in the first direction and to drive rotation of drive gears 122 of input gear assemblies 114, 118 similarly in the second direction. As a result of the driving of drive gears 122 of input gear assemblies 112, 116 similarly in the first direction, transition gear assemblies 132, 136 are driven to rotate in the second, opposite direction to, in turn, drive lead screw assemblies 152, 156 to rotate in the first direction, translating the hubs 164 thereof proximally and, thus, pulling articulation cables 38a, 38c proximally. As a result of the driving of drive gears 122 of input gear assemblies 114, 118 similarly in the second direction, transition gear assemblies 134, 138 are driven to rotate in the first direction to, in turn, drive lead screw assemblies 154, 158 to rotate in the second direction, translating the hubs 164 thereof distally and, thus, pushing articulation cables 38b, 38d distally. In this manner, jaw member 42 is approximated relative to jaw member 44 (FIGS. 1-2B).

The opposite rotational driving of input gear assemblies 112, 114 provides opposite inputs to first differential gear assembly 182 and, thus, no output. Likewise, the opposite rotational driving of input gear assemblies 116, 118 provides opposite inputs to second differential gear assembly 184 and, thus, no output. Since neither first differential gear assembly 182 nor second differential gear assembly 184 provides an output, third differential gear assembly 186 receives no input and, thus, provides no output.

With respect to opening jaw members 42, 44 of end effector assembly 40 (see FIGS. 1-2B), input from robotic surgical system 1000 (FIG. 3) is provided to drive rotation of drive gears 122 of input gear assemblies 112, 116 similarly in the second direction and to drive rotation of drive gears 122 of input gear assemblies 114, 118 similarly in the first direction. The result is the opposite as that detailed above with respect to approximating jaw members 42, 44 (FIGS. 1-2B). That is, hubs 164 of lead screw assemblies 152, 156 are translated proximally to pull articulation cables 38a, 38c proximally and hubs 164 of lead screw assemblies 156, 158 are translated distally to push articulation cables 38b, 38d distally, thereby pivoting jaw member 42 away from jaw member 44 (FIGS. 1-2B). Similarly as above, no output is provided from third differential gear assembly 186.

Figure 16:
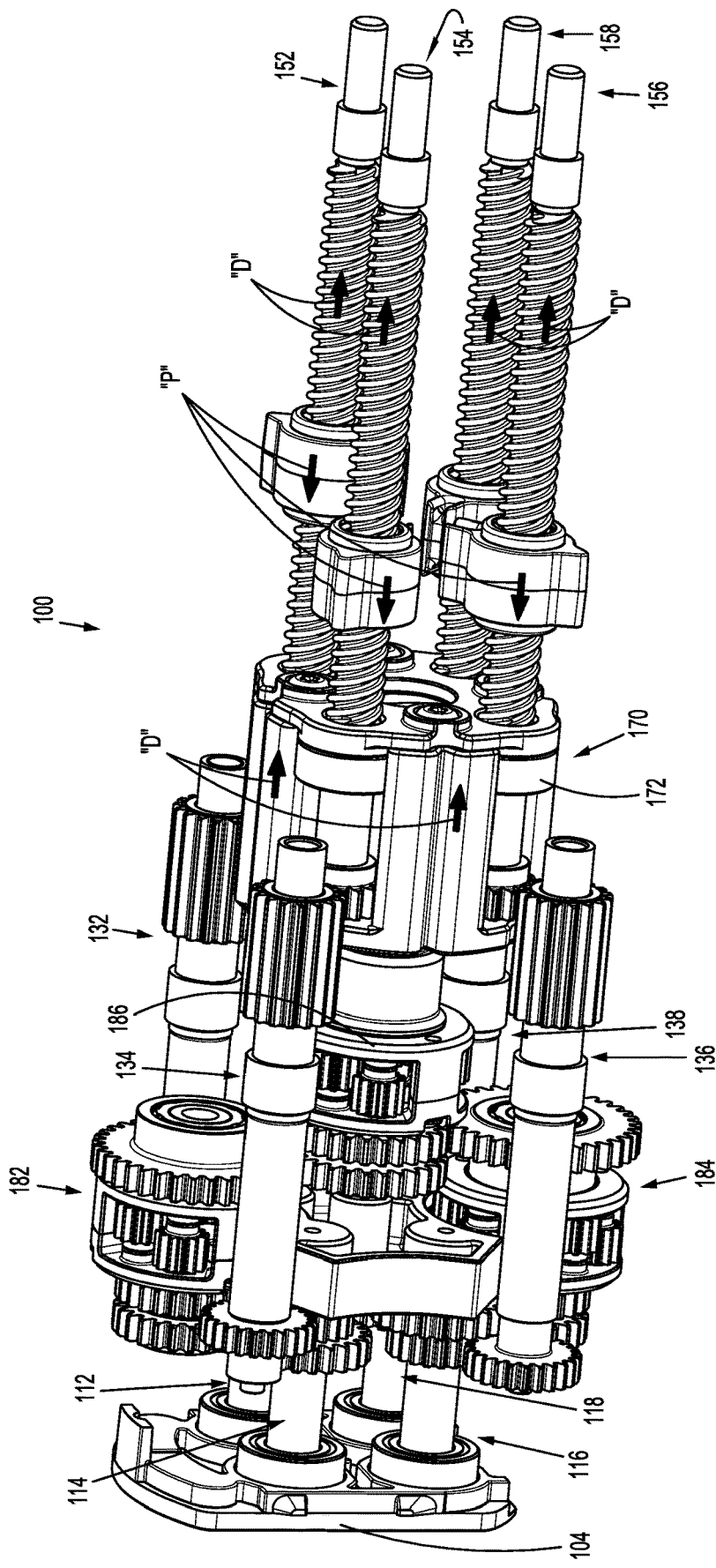
FIG. 16 is a perspective view of the gearbox assembly of FIG. 4 with the outer shell thereof removed, illustrating differential driving to advance a carriage of the gearbox assembly.
Figure 17:
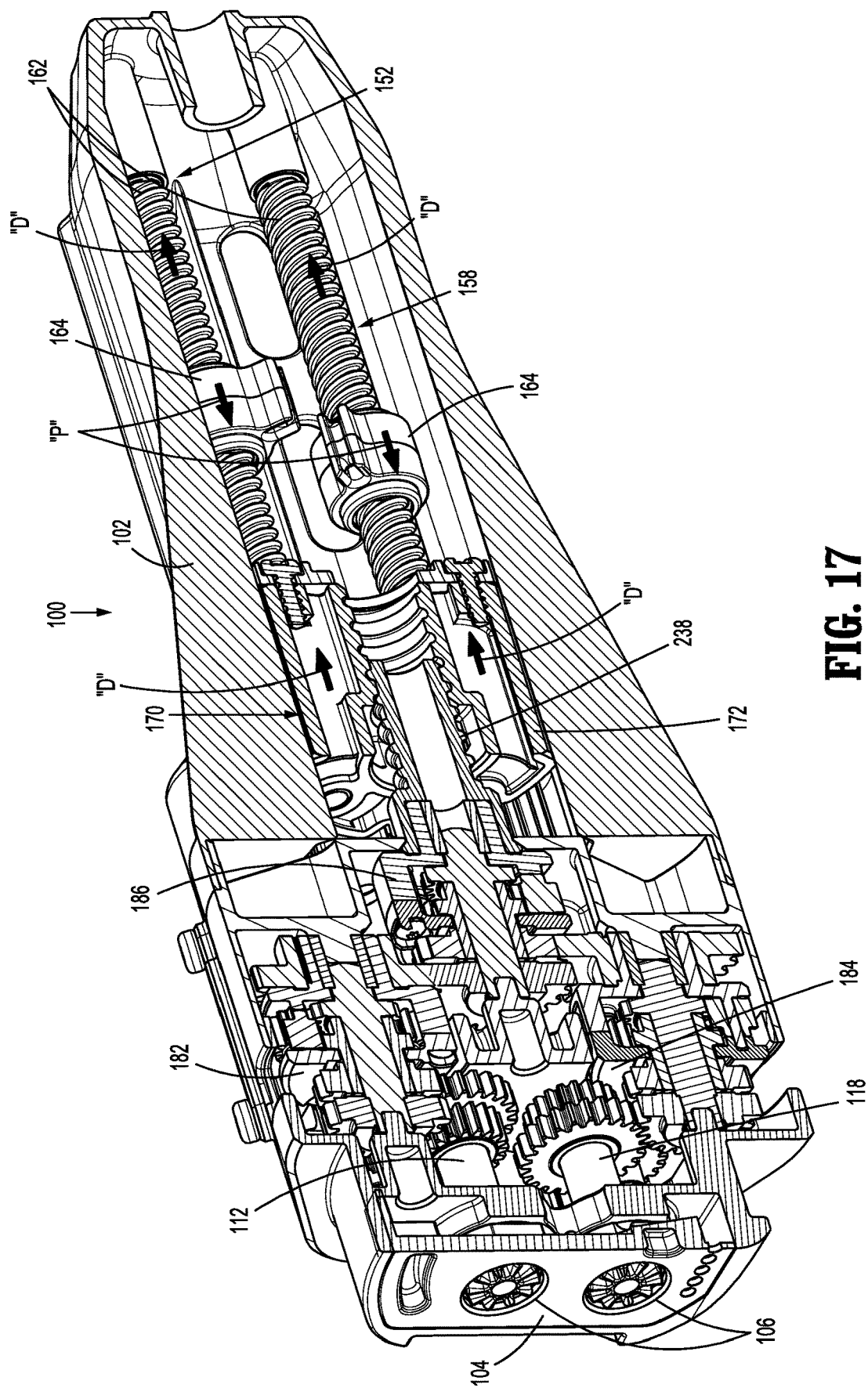
FIG. 17 is a longitudinal, cross-sectional view of the gearbox assembly of FIG. 4, illustrating differential driving to advance the carriage of the gearbox assembly.

Referring also to FIGS. 16 and 17, with respect to advancing knife blade 64 distally between jaw members 42, 44 of end effector assembly 40 (see FIGS. 1-2B), input from robotic surgical system 1000 (FIG. 3) is provided to drive rotation of drive gears 122 of input gear assemblies 112, 114, 116, 118 similarly. As a result, transition gear assemblies 132, 134, 136, and 138 are all driven to rotate similarly to, in turn, drive lead screw assemblies 152, 154, 156, 158 to all rotate similarly, for example, to translate the hubs 164 thereof proximally (see arrows "P" in FIGS. 16 and 17) and, thus, pull all of the articulation cables 38a, 38b, 38c, 38d proximally.

The similar rotational driving of input gear assemblies 112, 114, 116, 118 provides equal inputs to each of the first and second differential gear assemblies 182, 184 and, thus, each of the first and second differential gear assemblies 182, 184 provides an equal output to third differential gear assembly 186 which, as a result, likewise provides the same output. This output provided by third differential gear assembly 186, in turn, translates housing 172 of drive carriage assembly 170, for example, distally (see arrows "D" in FIGS. 16 and 17), equally and opposite to the proximal translation of hubs 164 (see arrows "P" in FIGS. 16 and 17).

As a result of the above, housing 172 of drive carriage assembly 170 is translated distally to urge knife cable 62 distally and, thus, to urge knife blade 64 distally between jaw members 42, 44 of end effector assembly 40 (see FIGS. 1-2B). Further, while hubs 164 are moving proximally along lead screw assemblies 152, 154, 156, 158, lead screw assemblies 152, 154, 156, 158 are themselves moving equally in the opposite direction, distally, such that there is no net effect on articulation cables 38a, 38b, 38c, 38d. Thus, knife blade 64 (FIG. 2B) is advanced without impacting articulation of end effector assembly 40 and/or pivoting of jaw members 42, 44 (see FIGS. 1-2B).

With respect to retracting knife blade 64 proximally from between jaw members 42, 44 of end effector assembly 40 (see FIGS. 1-2B), input from robotic surgical system 1000 (FIG. 3) is provided to drive rotation of drive gears 122 of input gear assemblies 112, 114, 116, 118 similarly but in the opposite direction as detailed above. Thus, the opposite as detailed above with respect to advancing knife blade 64 is effected. More specifically, knife blade 64 (FIG. 2B) is retracted without impacting articulation of end effector assembly 40 and/or pivoting of jaw members 42, 44 (see FIGS. 1-2B).

The movement of drive carriage assembly 170 to deploy or retract knife blade 64 (FIG. 2B) is effected without causing disengagement of lead screw gears 168 from respective elongated gears 146. That is, due to the elongated configuration of elongated gears 146, relative movement of lead screw gears 168 along respective elongated gears 146 maintains the meshed engagement therebetween.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:
1. A surgical instrument configured for use with a robotic surgical system, comprising:
  a housing;
  a shaft extending distally from the housing, the shaft including an articulating portion;
  an end effector assembly extending distally from the shaft and including first and second jaw members, at least the first jaw member movable relative to the second jaw member from a spaced-apart position to an approximated position to grasp tissue therebetween;
  a knife configured for translation between the first and second jaw members to cut tissue grasped therebetween; and
  a gearbox assembly disposed within the housing and operably coupled to the articulating portion of the shaft, the end effector assembly, and the knife, the gearbox assembly including four rotational input gears each adapted to receive a rotational input from a robotic arm, wherein the gearbox assembly is configured to independently articulate the end effector assembly about a first axis, articulate the end effector assembly about a second axis, move the at least one of the first or second jaw members relative to the other, and translate the knife between the first and second jaw members based upon the rotational inputs received by the four rotational input gears, wherein three of the first axis articulation, the second axis articulation, the moving, and the translation are achieved by actuating two different pairs of the four rotational input gears of the gearbox assembly in opposite rotational directions such that both gears in one of the two different pairs rotates in a first rotational direction and both gears in the other of the two different pairs rotates a second rotational direction opposite the first rotational direction, and wherein the other of the first axis articulation, the second axis articulation, the moving, and the translation is achieved by actuating all of the four rotational input gears of the gearbox assembly in the same manner.

2. The surgical instrument according to claim 1, further comprising a plurality of articulation cables operably coupled between the gearbox assembly and the articulating portion of the shaft, wherein the gearbox assembly is configured to selectively push or pull each of the plurality of articulation cables in a first manner to articulate the end effector assembly about the first axis in a first direction.

3. The surgical instrument according to claim 2, wherein the gearbox assembly is configured to selectively push or pull each of the plurality of articulation cables in a second, opposite manner to articulate the end effector assembly about the first axis in a second, opposite direction.

4. The surgical instrument according to claim 3, wherein the gearbox assembly is configured to selectively push or pull each of the plurality of articulation cables in a third manner to articulate the end effector assembly about the second axis in a third direction.

5. The surgical instrument according to claim 4, wherein the gearbox assembly is configured to selectively push or pull each of the plurality of articulation cables in a fourth manner opposite of the third manner to articulate the end effector assembly about the second axis in a fourth direction opposite of the third direction.

6. The surgical instrument according to claim 2, wherein at least two articulation cables of the plurality of cables are operably coupled to the first jaw member, and wherein the gearbox assembly is configured to selectively push or pull the at least two articulation cables in a fifth manner to move the first jaw member relative to the second jaw member from the spaced-apart position to the approximated position.

7. The surgical instrument according to claim 6, wherein the gearbox assembly is configured to selectively push or pull the at least two articulation cables in a sixth manner opposite of the fifth manner to move the first jaw member relative to the second jaw member from the approximated position back to the spaced-apart position.

8. The surgical instrument according to claim 2, further comprising a knife cable operably coupled between the gearbox assembly and the knife, wherein the gearbox assembly is configured to selectively push or pull the knife cable to translate the knife between the first and second jaw members.

9. The surgical instrument according to claim 1, wherein, in response to similar rotational inputs received by each of the four rotational input gears, the gearbox assembly is configured to translate the knife between the first and second jaw members.

10. The surgical instrument according to claim 1, wherein, in response to different rotational inputs received by two of the four rotational input gears, the gearbox assembly is configured to articulate the end effector assembly about a first axis, articulate the end effector assembly about a second axis, or move the at least one of the first or second jaw members relative to the other.

11. A surgical system, comprising:
a surgical robot including a robotic arm having four rotational outputs; and
a surgical instrument configured to couple to the robotic arm and receive the four rotational outputs therefrom; the surgical instrument including:
a housing;
a shaft extending distally from the housing, the shaft including an articulating portion;
an end effector assembly extending distally from the shaft and including first and second jaw members, at least the first jaw member movable relative to the second jaw member from a spaced-apart position to an approximated position to grasp tissue therebetween;
a knife configured for translation between the first and second jaw members to cut tissue grasped therebetween; and
a gearbox assembly disposed within the housing and operably coupled to the articulating portion of the shaft, the end effector assembly, and the knife, the gearbox assembly including four rotational input gears each adapted to couple to one of the four rotational outputs of the robotic arm,
wherein the gearbox assembly is configured to independently articulate the end effector assembly about a first axis, articulate the end effector assembly about a second axis, move the at least one of the first or second jaw members relative to the other, and translate the knife between the first and second jaw members based upon the rotational outputs provided by the robotic arm and received by the rotational input gears of the gearbox assembly, wherein three of the first axis articulation, the second axis articulation, the moving, and the translation are achieved by actuating two different pairs of the four rotational input gears of the gearbox assembly in opposite rotational directions such that both gears in one of the two different pairs rotates in a first rotational direction and both gears in the other of the two different pairs rotates a second rotational direction opposite the first rotational direction, and wherein the other of the first axis articulation, the second axis articulation, the moving, and the translation is achieved by actuating all of the four rotational input gears of the gearbox assembly in the same manner.

12. The surgical system according to claim 11, further comprising a plurality of articulation cables operably coupled between the gearbox assembly and the articulating portion of the shaft, wherein the gearbox assembly is configured to selectively push or pull each of the plurality of articulation cables in a first manner to articulate the end effector assembly about the first axis in a first direction.

13. The surgical system according to claim 12, wherein the gearbox assembly is configured to selectively push or pull each of the plurality of articulation cables in a second, opposite manner to articulate the end effector assembly about the first axis in a second, opposite direction.

14. The surgical system according to claim 13, wherein the gearbox assembly is configured to selectively push or pull each of the plurality of articulation cables in a third manner to articulate the end effector assembly about the second axis in a third direction.

15. The surgical system according to claim 14, wherein the gearbox assembly is configured to selectively push or pull each of the plurality of articulation cables in a fourth manner opposite of the third manner to articulate the end effector assembly about the second axis in a fourth direction opposite of the third direction.

16. The surgical system according to claim 12, wherein at least two articulation cables of the plurality of cables are operably coupled to the first jaw member, and wherein the gearbox assembly is configured to selectively push or pull the at least two articulation cables in a fifth manner to move the first jaw member relative to the second jaw member from the spaced-apart position to the approximated position.

17. The surgical system according to claim 16, wherein the gearbox assembly is configured to selectively push or pull the at least two articulation cables in a sixth manner opposite of the fifth manner to move the first jaw member relative to the second jaw member from the approximated position back to the spaced-apart position.

18. The surgical system according to claim 12, further comprising a knife cable operably coupled between the gearbox assembly and the knife, wherein the gearbox assembly is configured to selectively push or pull the knife cable to translate the knife between the first and second jaw members.

19. The surgical system according to claim 11, wherein, in response to similar rotational outputs provided by the robotic arm and received by the rotational input gears of the gearbox assembly, the gearbox assembly is configured to translate the knife between the first and second jaw members.

20. The surgical system according to claim 11, wherein, in response to different rotational outputs provided by the robotic arm and received by the rotational input gears of the gearbox assembly, the gearbox assembly is configured to articulate the end effector assembly about a first axis, articulate the end effector assembly about a second axis, or move the at least one of the first or second jaw members relative to the other.

* * * * *